(12) United States Patent
Babu et al.

(10) Patent No.: US 7,044,912 B2
(45) Date of Patent: May 16, 2006

(54) DIAGNOSTIC MEDICAL ULTRASOUND SYSTEM HAVING METHOD AND APPARATUS FOR STORING AND RETRIEVING 3D AND 4D DATA SETS

(75) Inventors: Sundar G. Babu, Bangalore (IN); Charles D. Emery, Renton, WA (US); Neerja Baru, Snoqualmie, WA (US); Sankaralingam Ramraj, San Jose, CA (US); Scott T. Luan, Woodhaven, NY (US)

(73) Assignee: Siemens Medical Solutions USA Inc., Malvern, PA (US)

( * ) Notice: Subject to any disclaimer, the term of this patent is extended or adjusted under 35 U.S.C. 154(b) by 294 days.

(21) Appl. No.: 10/650,618

(22) Filed: Aug. 28, 2003

(65) Prior Publication Data
US 2005/0049500 A1 Mar. 3, 2005

(51) Int. Cl.
*A61B 8/00* (2006.01)
(52) U.S. Cl. .................................................. 600/437
(58) Field of Classification Search ........ 600/407–472; 128/916; 707/1; 705/2
See application file for complete search history.

(56) References Cited

U.S. PATENT DOCUMENTS

| | | | |
|---|---|---|---|
| 5,272,625 A * | 12/1993 | Nishihara et al. | 707/1 |
| 5,546,807 A | 8/1996 | Oxaal et al. | |
| 6,128,002 A | 10/2000 | Leiper | |
| 6,137,487 A | 10/2000 | Mantha | |
| 6,370,413 B1 | 4/2002 | Alvarez et al. | |
| 6,377,162 B1 * | 4/2002 | Delestienne et al. | 340/286.07 |
| 6,422,474 B1 | 7/2002 | Gossweiler et al. | |
| 6,480,732 B1 | 11/2002 | Tanaka et al. | |

\* cited by examiner

*Primary Examiner*—Ali Imam

(57) ABSTRACT

A method and system is disclosed which permits a user to save user defined viewing configuration, also referred to as a bookmark as a separately manipulatable or transferable entity without altering the underlying image data and maintaining, where desired, the association between the bookmark 200 and the underlying source image data. The disclosed system and method act to save the bookmark by saving the succession of system inputs, which, in conjunction with the system characteristics and system parameters, achieve the desired viewing configuration. Thereby, the disclosed system and method permits review of the inputs used to manipulate the image to confirm the process by which a diagnosis or anatomical measurement was made, permits the replay of a sequence for presentation or training purposes to effectively demonstrate not only the end result, but the methodology as well. The disclosed system and method further permits the user to save the system parameters as set for a desired given viewing configuration of a 4D image sequence in addition to or in lieu of saving the system inputs. In this way, the desired viewing configuration is preserved while maintaining the integrity of the underlying image data. In addition, the disclosed system and method further permit the user to maintain or terminate the association of the bookmark 200 with the entirety of the source image data, or just a portion thereof.

59 Claims, 4 Drawing Sheets

DIAGNOSTIC MEDICAL ULTRASOUND SYSTEM HAVING METHOD AND APPARATUS FOR STORING AND RETRIEVING 3D AND 4D DATA SETS

BACKGROUND

Diagnostic medical imaging systems, such as diagnostic medical ultrasound imaging systems, are widely used for medical diagnostic applications. In more complex systems, three-dimensional (3D) volume data of anatomical structures can be acquired, as well as the typical two-dimensional (2D) images. In such systems, the acquired 3D volume data can be used to view virtual anatomical structures in different configurations by manipulating the 3D volume data to display 2D images on a display coupled with the imaging system. As an example, the 3D volume data can be viewed by slicing through the displayed volume data at some arbitrary user-specified location or by using one of the available volume rendering algorithms. In even more complex systems, sequences of 3D volume data can be acquired over a period of time, also referred to as four dimensional (4D) imaging. In such systems, not only can the acquired data of each 3D volume be manipulated, but the time based sequence of 3D volumes may also be manipulated to view dynamic or temporally sensitive characteristics of the imaged anatomical structures.

A "3D volume" is defined herein as a construction of imaging information relating to three dimensions of a target. As one example, a 3D volume may be formed by assembling a number of acquired frames (slices or voxels) of two dimensional pixel data, with each frame representing a cross section along a different plane through the target volume. Combining the frames of pixel data is one approach to providing a 3D volume of 3D volume data. A "4D ultrasound sequence" typically includes a sequence of 3D volumes associated by being acquired over a defined period of time.

For example, during an ultrasound examination using a conventional 3D diagnostic medical ultrasound imaging system, one or more 3D ultrasound volumes (of B, power, color, etc. information) from an anatomical structure of a patient may be acquired by a sonographer. Each acquired 3D volume, or the acquired 4D sequence of volumes, can then be manipulated in different configurations to render one or more 2D images on the display from the 3D volume data via the input and/or manipulation of a set of viewing parameters. Each viewing configuration of the 3D volume data requires the input or manipulation of a set of viewing parameters to define the desired rendering. These 2D images are then typically saved for subsequent review for evaluation or diagnosis. In general, the 2D images are captured and saved in a sequential manner during operations in which the 3D volume data is manipulated to render a different viewing configuration for each subsequent 2D image. The underlying 3D volume data for the saved 2D images may also be saved for subsequent retrieval.

If a particular 3D volume is saved, the sonographer can capture additional 2D images from that 3D volume and/or continue diagnostic review of that data at a later time. However, the sonographer will have to re-enter the viewing parameters to manipulate the 3D volume data to a desired viewing configuration, which would typically be the viewing configuration that was defined when the last 2D image was captured and saved. It can take the sonographer some time to set the right parameters for the desired viewing configuration. In some cases, however, it may also be impractical and/or impossible for the sonographer to set the exact viewing configuration from the previously saved 2D image in order to continue with their review/evaluation. Thus, capturing additional 2D images from saved 3D volume data can be a tedious task. Due to this inconvenience, a sonographer is motivated to use the examination time to capture and save all of the 2D images that may be of interest at a later time. Of course, this prolongs the duration of the examination as well as increases burden on resources, such as image/data storage resources.

Accordingly, there is a need for a diagnostic medical imaging system, such as a diagnostic medical ultrasound imaging system, and a method for managing the saved 2D viewing configurations, their underlying 3D volume(s), or 4D sequence(s) and the relationship or association of the viewing configurations and 2D images with the 3D volume or 4D sequence, such that it is more convenient and efficient to acquire and store additional 2D images from the 3D volume data and/or continue diagnostic review of this data after the initial imaging examination.

SUMMARY

The present invention is defined by the following claims, and nothing in this section should be taken as a limitation on those claims. By way of introduction, the preferred embodiments described below relate to an apparatus for managing image data acquired with a first diagnostic medical imaging system, the first diagnostic medical imaging system comprising a first display, the image data comprising a first arrangement. The apparatus includes: first display logic coupled with the first display and operative to display the image data on the first display having a second arrangement as a function of the first arrangement. In addition, the apparatus include first input logic coupled with the first display logic and operative to receive a sequence of inputs, the sequence of inputs operative to cause the first display logic to manipulate the displayed image data from the second arrangement to a third arrangement displayed on the first display without substantially altering the first arrangement. Further, the apparatus includes first store logic coupled with the first display logic and the first input logic and operative to store the received sequence of inputs in a first memory coupled with the first store logic, the stored sequence of inputs capable of being retrieved from the first memory and automatically applied to the first display logic to cause the first display logic to manipulate the displayed image data having the second arrangement to realize the third arrangement displayed on the first display without substantially altering the first arrangement.

The preferred embodiments further relate to an apparatus for managing image data acquired with a first diagnostic medical imaging system, the first diagnostic medical imaging system comprising a first display and a first plurality of display parameters, each of the display parameters further comprising a value, the value of each of the first plurality of display parameters operative to control an arrangement of the image data as displayed on the display. The apparatus includes first display logic coupled with the first display and operative to display the image data on the first display, the displayed image data comprising a sequence of three dimensional volumes, each three dimensional volume of the sequence of three dimensional volumes having been incrementally acquired over a period of time, the displayed image data further having a first arrangement displayed on the display based on the image data and at least one of the values of the first plurality of display parameters. In addition, the apparatus includes first input logic coupled with the first display and operative to receive input, the input operative to alter the value of at least one of the first plurality of display parameters, whereby the first display logic is operative to manipulate the displayed image data from the first arrangement displayed on the display to a second arrangement displayed on the display based on the altered value, without substantially altering the image data. Further, the apparatus includes first store logic coupled with the first input logic and the first display logic and operative to store at least the altered value in a first memory coupled with the first store logic, wherein the stored altered value is capable of being automatically applied to the displayed image data having the first arrangement to realize the second arrangement on the display without substantially altering the image data.

The preferred embodiments further relate to a method of managing image data acquired with a first diagnostic medical imaging system, the first diagnostic medical imaging system comprising a display, the image data comprising a first arrangement. In one embodiment, the method includes: displaying the image data on the display, the displayed image data having a second arrangement based on the first arrangement; receiving a sequence of inputs, the sequence of inputs operative to manipulate the displayed image data from the second arrangement to a third arrangement, without substantially altering the first arrangement; and recording the sequence of inputs, the recorded sequence of inputs being capable of being automatically applied to the displayed image data having the second arrangement to realize the third arrangement without substantially altering the first arrangement.

The preferred embodiments further relate to a method of managing image data acquired with a first diagnostic medical imaging system, the first diagnostic medical imaging system comprising a display and a plurality of display parameters, each of the display parameters further comprising a value, the value of each of the plurality of display parameters operative to control an arrangement of the image data as displayed on the display. In one embodiment, the method includes: displaying the image data on the display, the displayed image data comprising a sequence of three dimensional volumes, each three dimensional volume of the sequence of three dimensional volumes having been incrementally acquired over a period of time, the displayed image data further having a first arrangement displayed on the display based on the image data and at least one of the values of the plurality of display parameters; receiving input operative to alter the value of at least one of the plurality of display parameters, whereby the displayed image is manipulated from the first arrangement displayed on the display to a second arrangement displayed on the display based on the altered value, without substantially altering the image data; and recording at least the altered value, wherein the recorded altered value is capable of being automatically applied to the displayed image data having the first arrangement to realize the second arrangement on the display without substantially altering the image data.

Further aspects and advantages of the invention are discussed below in conjunction with the preferred embodiments.

DETAILED DESCRIPTION OF THE DRAWINGS AND PRESENTLY PREFERRED EMBODIMENTS

A method and system is disclosed which permits a user to save a user defined viewing configuration, also referred to as a bookmark 200, as a separately manipulatable or transferable entity without altering the underlying image data and maintaining, where desired, the association between the bookmark 200 and the underlying source image data. The disclosed system and method act to save the bookmark 200 by saving the succession of system inputs 202, which in conjunction with the system characteristics and system parameters, achieve the desired viewing configuration. Thereby, the disclosed system and method permits review of the inputs used to manipulate the image to confirm the process by which a diagnosis or anatomical measurement was made and permits the replay of a sequence for presentation or training purposes to effectively demonstrate not only the end result, but the methodology as well. The disclosed system and method further permits the user to save the system parameters as set for a desired given viewing configuration of a 4D image sequence(s) in addition to or in lieu of saving the system inputs. In this way, the desired viewing configuration is preserved while maintaining the integrity of the underlying image data. In addition, the disclosed system and method further permit the user to maintain or terminate the association of the bookmark 200 with the entirety of the source image data, or just a portion thereof. Further, in maintaining an association of the bookmark 200 with the underlying image data as well as permitting multiple bookmarks 200 to be associated with the same underlying image data, unnecessary replication of image data is avoided.

Figure 1:
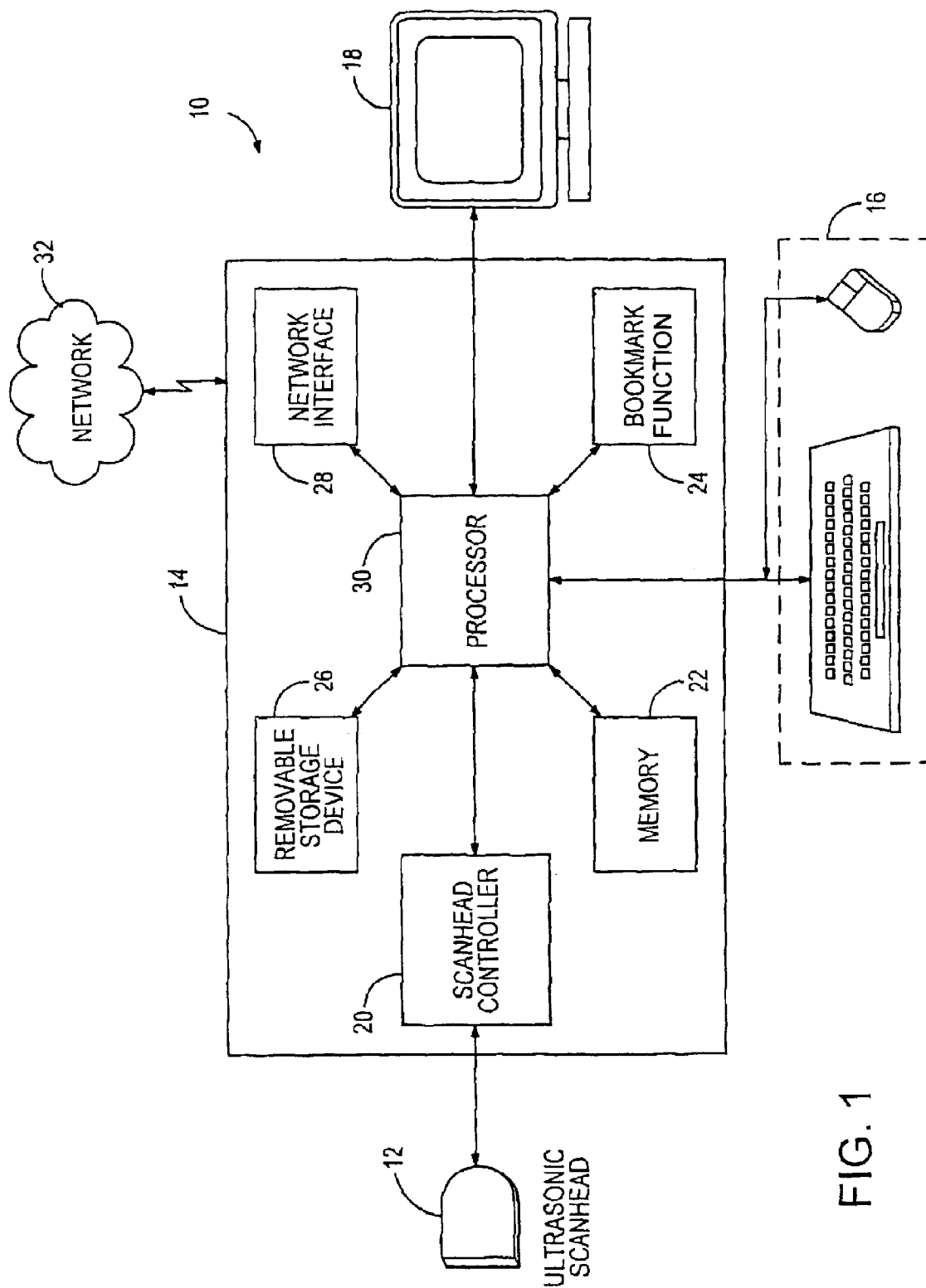
FIG. 1 depicts a block diagram of an exemplary diagnostic medical imaging system for use with the disclosed embodiments.

FIG. 1 shows a block diagram of an ultrasound imaging system 10 in accordance with one disclosed embodiment. The ultrasound imaging system 10 may comprise a Cypress Echocardiography System, the Acuson Sequoia™ Ultrasound platform or the Sonoline Antares™ Ultrasound Platform, manufactured by Siemens Medical Solutions USA, Inc., located in Malvern, Pa., and executing a software program in accordance with the disclosed embodiments. Alternatively, the imaging system 10 may comprises a review workstation executing software which allows a user to view and manipulate image data acquired elsewhere, such as a Cypress Review Station. Cypress Review Stations include standard Microsoft Windows based personal computers executing the Cypress Viewer application software, manufactured by Siemens Medical Solutions USA, Inc., located in Malvern, Pa., capable of viewing patient study files acquired with diagnostic medical imaging systems. It will be appreciated that the disclosed embodiments may be implemented in software, hardware or a combination thereof and are not limited in application to diagnostic medical ultrasound imaging systems but may also be used with other diagnostic medical imaging systems such as magnetic resonance imaging ("MRI") systems, computed tomography ("CT") systems, and x-ray imaging systems, or other imaging systems which acquire 3D volume data over time. The exemplary imaging system 10 is designed to acquire one or more 3D ultrasound volumes during an ultrasound examination by transmitting ultrasound waves and receiving echoes of the transmitted ultrasound waves that are reflected from the anatomical structure being examined. In one embodiment, the imaging system 10 is compatible with the Digital Imaging and Communication in Medicine ("DICOM") imaging standard, published by the American College of Radiology ("ACR") and the National Electrical Manufacturers Association ("NEMA"), located in Rosslyn, Va., which specifies standardized protocols for image data storage and communication for diagnostic medical imaging systems.

As used herein, a three dimensional ("3D") volume includes a multiframe image wherein each frame represents a slice of the volume. The number of frames which make up the volume is equal to the number of voxels in the volume. A voxel is a volume element similar to a pixel, e.g. picture element, wherein the number of voxels is a designation of the sampling of the 3D volume in the Z dimension and the number of pixels and number of lines specify the sampling of the individual frames of the 3D volume in the X and Y dimensions respectively, the X, Y and Z dimensions all being perpendicular to each other. In one embodiment, a four dimensional ("4D") sequence refers to a collection of 3D volumes related by time, e.g. acquired over a period of time, either contiguous or non-contiguous. In an alternate embodiment, a 4D sequence refers to image data otherwise categorized by any four parameters of interest, such as a sequence of 2D images acquired over time, wherein one or more characteristics of the received image data vary as a function of time, intensity and/or position. For example, a 4D sequence may include a 2D color Doppler flow image used to render a representation of fluid flow in a portion of a subject. In this example, the four parameters of the 4D sequence include the vertical and horizontal (x and y) position of the detected flow within the image, time and the flow direction, velocity and/or intensity as represented by varying color intensity.

A snapshot is a two dimensional ("2D") representation, e.g. a 2D bit map, of a 2D acquired image or sequence of images, a portion of a 3D volume or a portion of a 4D sequence. A snapshot is typically a capture of the image as currently visually represented on a 2D display coupled with the imaging system 10, including any manipulation or augmentation as described below. Herein, the phrase "coupled with" is defined to mean directly connected to or indirectly connected through one or more intermediate components. Such intermediate components may include both hardware and software based components. A 2D snapshot may include the illusion of a 3D representation. Once captured, the snapshot data is "disconnected", e.g. copied, from the source image data from which it was captured, and while the snapshot is capable of being manipulated on its own, any source image data not visually present in the captured 2D representation at the time of capture, is typically unavailable in the snapshot at a later time. In an alternate embodiment, a 3D snapshot is a capture of a 3D image of a particular 3D volume, or transition between 3D volumes, in a particular configuration or at a particular instant of time, of a sequence of one or more volumes acquired over time. A 3D snapshot captures all of the volumetric data at the instant of time, irregardless of what is being currently two-dimensionally represented on the display. Similarly, once captured, the 3D snapshot data is "disconnected", e.g. copied, from the source image data from which it was captured, and while the snapshot is capable of being manipulated on its own, any source image data not visually present in the captured 3D representation at the time of capture, is typically unavailable in the snapshot at a later time.

An acquired 3D volume or 4D sequence may be manipulated to capture and save 2D or 3D snapshots. For example, the user may rotate a particular 3D volume so as to bring a particular anatomical feature perspectively into the foreground of the 2D image, display a particular plane or slice through the volume (at a fixed or arbitrary angle relative to a given origin), the user may mark or otherwise augment the image to highlight or isolate a particular feature(s) or event(s) and/or the user may alter the playback speed of a subset of image data, such as a sequence of 3D volumes, of a 4D sequence, or freeze the playback to highlight or isolate a particular transition from one 3D volume to another 3D volume of the sequence, or the user may create a composite image from multiple portions of the source image data, etc. It will be appreciated that there are many ways in which the user may manipulate the displayed image data such as by manipulating image presentation, composition, rendering position, organization, annotation, augmentation, transformation, and/or rotation.

A viewing configuration, also referred to herein as an arrangement, is the collection of imaging system characteristics, system parameters and aggregation of system inputs which, in conjunction with the source image data, control the image rendering functionality of the system 10 to create a particular displayed 2D representation on the display 18. A viewing configuration differs from a snapshot, in that a viewing configuration is an interpretation of the entirety of the source image data, rather than a copy or interpretation of a subset of the source image data, and can therefore be further manipulated to reveal features from the source image data not currently present in the currently displayed 2D representation, thereby creating a new displayed 2D representation.

The source image data, herein also referred to as the raw image data, includes the actual 2D, 3D or 4D image data acquired by the imaging system. The source image data further comprises a default viewing configuration, or arrangement, which defers to the imaging system characteristics of the acquiring system 10 and, in some embodiments, the default values of the system parameters at the time the image data is captured. These parameters become characteristics of the data and control the default 2D view of the data, in concert with the default values of the system parameters currently set when the data is first rendered to the display 18 by the imaging system's 10 rendering functionality. As will be described in more detail below, subsequent inputs may then be used to manipulate this default viewing configuration into other viewing configurations.

Imaging system 10 characteristics include the capabilities of the imaging system 10 used to acquire the source image data or the imaging system 10 currently being used to view that source image data. Such characteristics include the processing speed, display hardware characteristics such as maximum resolution, color depth, etc,. and other implicit or explicit characteristics, capabilities and/or limitations of the actual system hardware or software.

System parameters include user or software definable settings, which may or may not be limited by the imaging system 10 characteristics, such as hardware or software/operating system environment variables, which contribute to a particular viewing configuration. System parameters may derive their value, i.e. the actual setting of the parameter, from system inputs described below, or may be predetermined, such as by having default values or values derived from the imaging system 10 characteristics described above. System parameters include pre-set operational values, such as fonts or display resolution, or measurement settings, such as measurement units. System parameters may further include image orientation, geometry, rendering algorithm (e.g., surface rendering and arbitrary slicing), colormaps, imaging acquisition parameters, and other common parameters that are used to view acquired images. System parameters may also include real time volumetric and image parameters, such as chronological parameters or playback speed. The exact types of viewing parameters used are not critical to the disclosed embodiments.

System inputs include externally provided data such as inputs received from a user via the system user interface 16, inputs received over a network 32 or other communications medium, and inputs generated by other software applications executing locally or remotely which are external to the software and/or hardware responsible for rendering the currently displayed viewing configuration. System inputs received via the user interface 16 may include inputs specifically directed to the rendering functionality of the system 10 or inputs directed to another application or functionality of the system 10 which then controls the rendering functionality in response to the given inputs. Exemplary system inputs include commands to place markers in an image, such as graphic markers used to highlight or isolate portions of a displayed 2D image, or other user directed image annotation or augmentation. Exemplary system inputs also include commands to designate beginning, ending and primary 3D volumes of a 4D sequence or user defined settings of system parameters as described above. As will be discussed below, system inputs may be captured at the input level, i.e. a capture of the actual input, or may be captured at a lower level within the operating system of the imaging system 10, such as by capturing the operating system commands or events triggered by the input which achieve the desired result, such as the OpenGL or DirectX command(s). For example, where a user selects an option from a graphic user interface pull down menu, the actual pointer movement and option selection may be captured or the low level command to select the option may be captured instead. In one embodiment, the system inputs may include inputs relating to position and/or orientation of the imaging device, e.g. the ultrasound transducer, the subject being imaged, or other 2D or 3D based input device used to manipulate the displayed image.

The disclosed embodiments permit users to save particular viewing configurations and their association with the underlying source image data, herein referred to as a "bookmark" 200, related to a displayed 2D image such that the particular viewing configuration, including the displayed 2D image, can be recreated, or rather restored, at a later time. This is distinguished from saving a snapshot. A snapshot is a static capture of the currently displayed 2D image or 3D volume rendered as a consequence of the current viewing configuration. A snapshot is a capture of a subset of the source image data that is independent of that source image data which was manipulated to achieve the captured 2D image or 3D volume. As describe above, a snapshot may be incapable of being further manipulated to reveal or derive other data or information present in the source data but not captured in the snapshot. However, a bookmark 200 may be used to recreate or restore a particular viewing configuration of the entirety of the source image data, including the resultant 2D image or 3D volume, thereby returning the user to the state at which the bookmark was saved, and allowing further manipulation to other viewing configurations, revelation of other acquired image data and/or derivation of additional information.

In one embodiment, the bookmark function 24 acts to automatically save a bookmark 200, as described below, whenever the system 10 encounters an error condition, loss of function or otherwise loses operating power, whether intentionally or unintentionally, while image data is being acquired and/or reviewed. Where an error condition or disabling event is indicated, the bookmark function 24 may act to save a bookmark 200 of the current viewing configuration prior to loss of function or power. In one embodiment, a temporary bookmark 200 is maintained and updated with each system input received, and/or at regular intervals, in anticipation of a potential loss of function/power. Upon restoration of system 10 power or function, the bookmark function 24 may automatically act to restore the last saved viewing configuration from the "emergency" bookmark 200 or inform the user that such a bookmark 200 is available.

In one embodiment, the system 10 permits the user to save the viewing configuration, i.e. bookmark 200, used to create a particular displayed 2D image. In an alternate embodiment for use with a 4D sequence, the user may save only the system parameters 204 that were used to manipulate the underlying 3D volumes to a specific viewing configuration. In yet another alternative embodiment, the user may also save a 2D or 3D snapshot 208 coincident with the current viewing configuration. The saved viewing configuration, system parameters 204 or snapshot 208 may or may not include information 210 identifying the source image data. The saved viewing configuration allows a user to retrieve the underlying source image data, if saved and identified, in the specific viewing configuration into which the source image data was manipulated when the viewing configuration was captured and saved. Thus, the user of the imaging system 10 does not have to re-create the viewing configuration to manipulate the source image data into the previously set configuration, alter the source image data with their manipulations or create a copy of the source image data as manipulated. This essentially permits the user to return to where they last left off in a particular review session. Further, the viewing configuration is saved independent of, and without altering, the source image data. This permits subsequent access to the source image data to perform alternative analyses by the same or a different user, verification and/or editing of the viewing configuration and use of the viewing configuration with other source image data, as will be described below. In addition, by not having to save a copy of the source image data, as manipulated, to create the bookmark 200, resources, such as image data storage space, are conserved. It will be appreciated that while the bookmark 200/viewing configuration data is independent of the source image data, the bookmark data and the source image data may be stored in a common data structure. For example, data structures adhering to the DICOM standard, discussed above, may be used to store both the underlying source image data and the bookmark 200.

Figure 3:
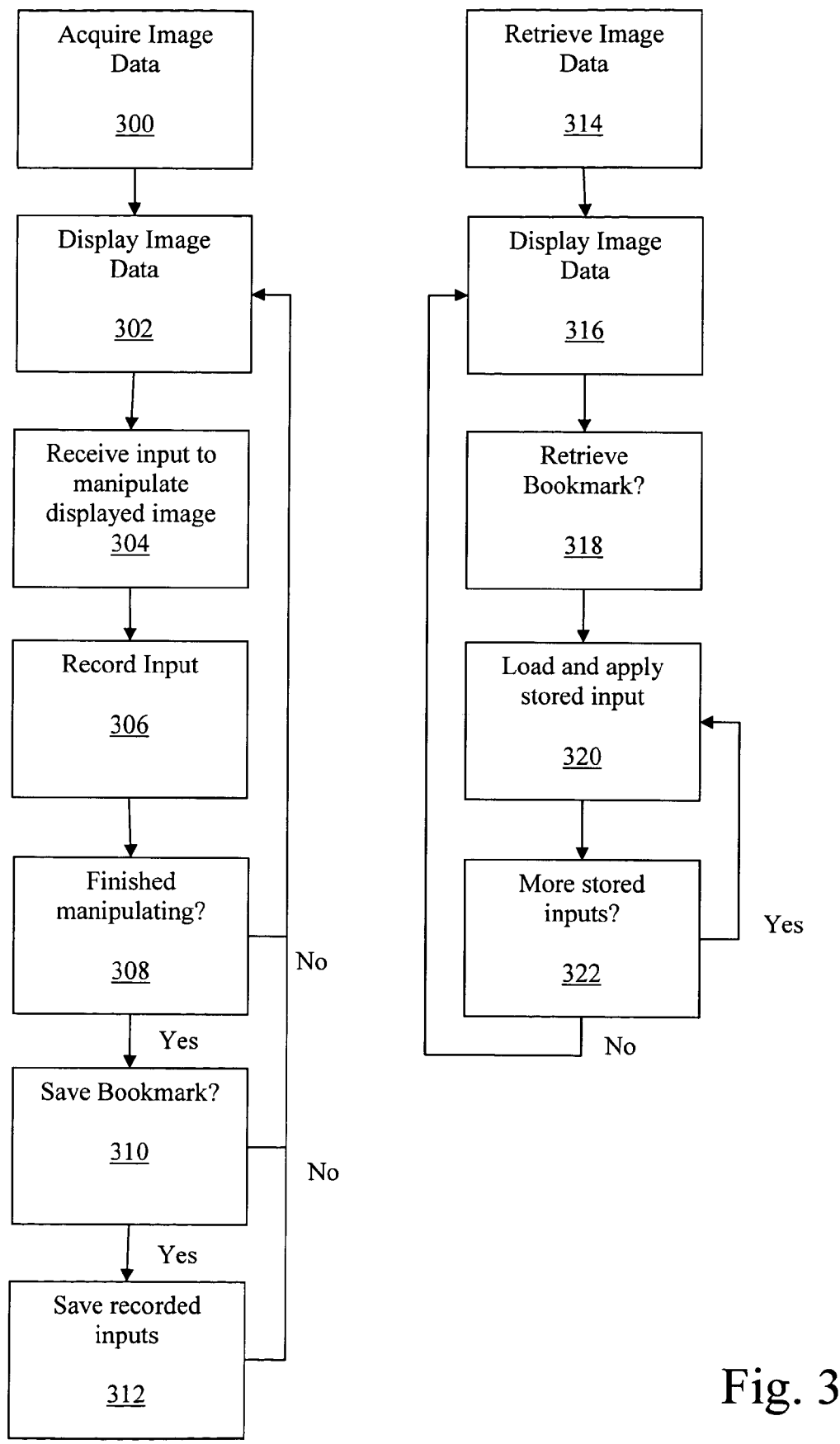
FIG. 3 depicts flow charts detailing creation and use of bookmarks according to one embodiment.

FIG. 3 shows flow charts detailing the basic process by which a user creates and uses bookmarks 200 according to one embodiment, and described in more detail below. The user uses the imaging system 10 to acquire (block 300) and display images (block 302). The user then provides inputs 202 to manipulate the acquired image data (block 304) causing the displayed 2D representation to change. These inputs 202 are recorded (block 306). Once the user has finished manipulating the image data or reached a point where they wish to create a bookmark 200 (block 308) they may indicate to the system 10 to create a bookmark (block 310) wherein the system then saves the recorded inputs 202 as described below. To utilize the bookmark 200, the user retrieves the source image data, if necessary (block 314), which may cause a 2D representation of the image data to be displayed according to the default viewing configuration (block 316). The user may then select to retrieve a bookmark 200 (block 318), which causes the recorded system inputs 202 to be read from the bookmark file and applied to the source image data to restore the saved viewing configuration (blocks 320 and 322). In an alternate embodiment, the user may retrieve the bookmark 200 first, prior to loading the source image data.

Figure 4:
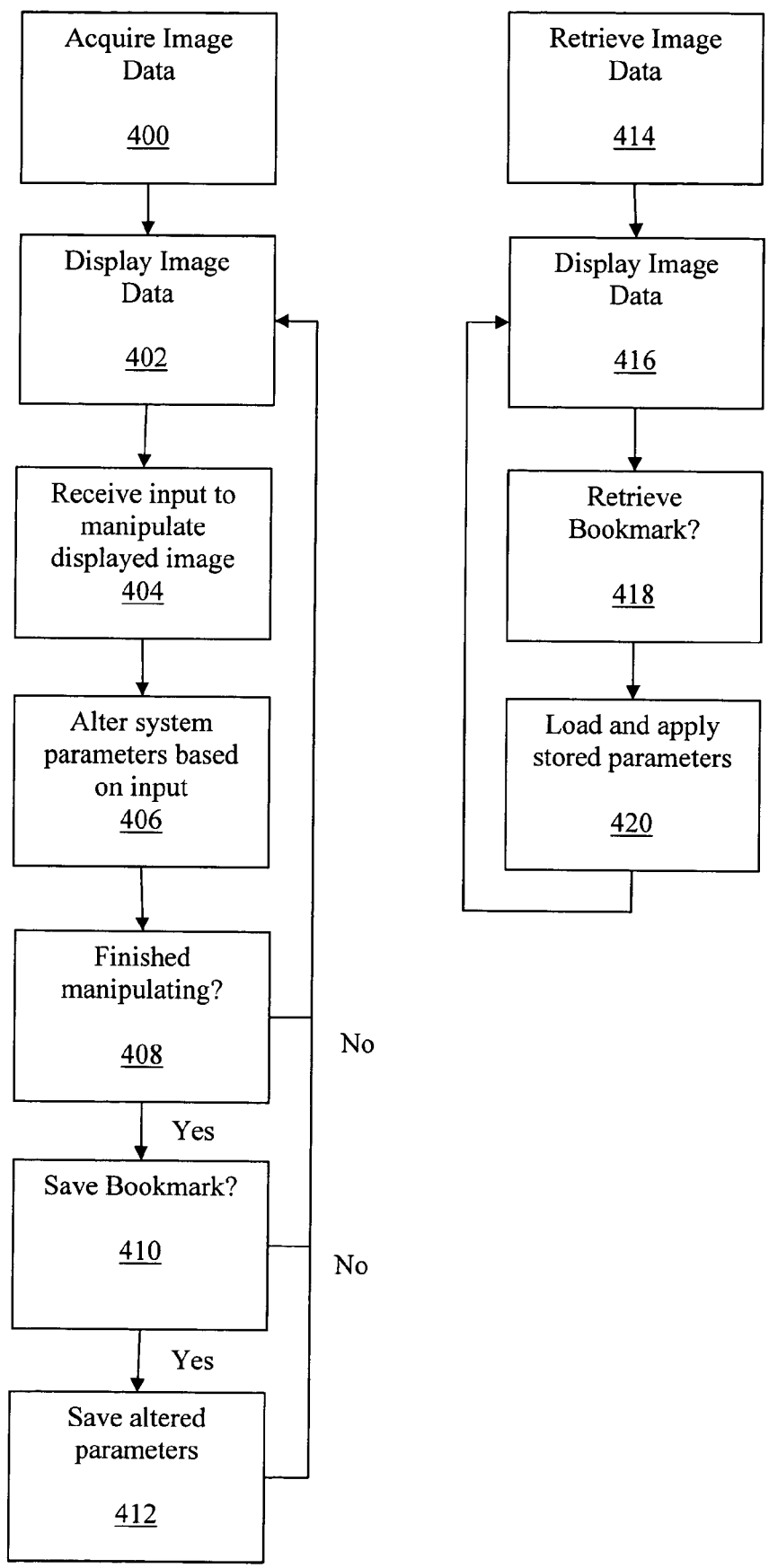
FIG. 4 depicts flow charts detailing creation and use of bookmarks according to an alternate embodiment.

FIG. 4 shows flow charts detailing the basic process by which the user creates and uses bookmarks 200 according to an alternate embodiment, which is also described in more detail below. The user uses the imaging system 10 to acquire (block 400) and display images (block 402). The user then provides inputs 202 to manipulate the acquired image data (block 404) which alters the system parameters controlling the displayed 2D representation and causing it to change (block 406). Once the user has finished manipulating the image data or reached a point where they wish to create a bookmark 200 (block 408) they may indicate to the system 10 to create a bookmark (block 410) wherein the system then saves the altered system parameters 204 as described below. To utilize the bookmark 200, the user retrieves the source image data, if necessary (block 414) which may cause a 2D representation of the image data to be displayed according to the default viewing configuration (block 416). The user may then select to retrieve a bookmark (block 418) which causes the recorded system parameters 204 to be read from the bookmark file and applied to the source image data to restore the saved viewing configuration (block 420).

The exemplary ultrasound imaging system 10 includes an ultrasonic scan-head 12, a processing unit 14, an input device 16, and a display device 18. The ultrasonic scanhead 12 includes an array of piezoelectric elements that generates ultrasound waves in response to electrical signals of proper voltage and frequency. As is well known in the art, the piezoelectric element array of the scanhead 12 also generates electrical signals in response to mechanical vibrations caused by return echoes of the ultrasound waves. These return echoes are processed by the processing unit to image an anatomical structure of interest in 2D, 3D or 4D as described and rendered to the display 18 by the system 10 rendering functionality (not shown). These processed return echoes comprise the source image data.

The input device 16 of the system 10 includes a standard computer keyboard and a pointing device, as shown in FIG. 1. The input device 16 is used as a user interface to control the functions of the system, such as initiating ultrasound imaging, acquiring 2D, 3D or 4D image data for a particular anatomical structure, manipulating the acquired image data, capturing and saving bookmarks and/or snapshots from the manipulated image data, and retrieving the underlying source image data for a designated bookmark or snapshot. In one embodiment, the input device 16 is used to interact with a graphic user interface executing on the processor 30 and displayed on the display device 18. The display device 18 of the system may be a conventional computer monitor, such as a CRT or an LCD monitor. In an alternate embodiment, the display device 18 may include a three dimensional display capable of displaying three dimensional images to the user.

The processing unit 14 is designed to perform various signal processing and other procedures that are required for proper operation of the ultrasound imaging system and implementation of the disclosed embodiments. Included in the processing unit 14 are a scanhead controller 20, memory 22, a bookmark function 24, a removable storage device 26, a network interface 28, and a processor 30. The scanhead controller is operatively connected to the ultrasonic scanhead 12 to control the transmitting and receiving operations of the scanhead 12. The memory 22 may be a volatile or non-volatile memory, such as a random access or flash memory and/or standard hard disk drive that is commonly found in a typical personal computer. The removable storage device 26 may utilize one of a number of removable storage media that are currently available, such as a writeable CD, a DVD, or a magneto-optical storage medium. Alternatively, the removable storage device 26 may be an on-system storage device, such as a hard disk drive or a wired/wireless Personal Digital Assistant ("PDA"). The network interface 28 may include a modem or an Ethernet interface that allows the system 10 to be connected to a network 32. The network 32 may be any type of network, wired or wireless, such as a LAN, a WAN, or the Internet.

In one embodiment, the bookmark function 24 of the processing unit 14 is configured to operate with the processor 30 to automatically save the current viewing configuration used to manipulate the underlying source image data to a specific displayed 2D image, at the initiation of the user via the input device 16 or completely autonomously. In one embodiment, the bookmark function 24 is a software program executing on the processor 30, and may be a function of the operating system available to all applications executing on the system 10 or available only in specific imaging applications. The bookmark function 24 operates to capture all system inputs, described above, as they are received by the image rendering functionality of the system 10, as well as monitor the state of system characteristics and parameters. The captured system inputs 202 are maintained in a data structure which stores both the input itself and the relationship of that input to the other captured inputs, e.g. the order/sequence of inputs. In one embodiment, information such as the date and time that the input was entered, the real time elapsed between inputs, or events or other data existing concurrently with the input, may also be captured. In yet another embodiment, the values of the system characteristics and system parameters 204 at the time of the input are also captured, either before or after the input causes its intended effect on the system 10.

After source image data of an anatomical structure has been acquired by the imaging system 10, be it 2D, 3D or 4D image data, whether acquired live from a subject or retrieved from local or remote storage, the source image data can be manipulated into a desired viewing configuration, if not so already, by the user or other software via the provision of system inputs. This viewing configuration, prior to being saved as a bookmark 200, is referred to as a "potential bookmark." Once a desired viewing configuration is achieved, the user can choose to "bookmark" the viewing configuration, such as by selecting a graphic user interface element displayed on the display 18 or otherwise indicating that a bookmark 200 should be saved via the input 16. The bookmark function 24 then stores the captured system inputs as a bookmark 200 file. As described above, other data, such as the current system characteristics and system parameters and/or the system characteristics and system parameters 204 coincident with each saved input, may also be saved in the bookmark file. The user is then free to continue manipulating the viewing configuration and saving additional bookmarks. In one embodiment, each bookmark file stores the aggregated system inputs captured over the course of the manipulation from the default viewing configuration of the source image data, as described above, to the current configuration. In an alternate embodiment, as the user creates subsequent viewing configurations, only the incremental system inputs, from one viewing configuration to the next, are captured. In such an embodiment, the incremental system inputs may be stored in a single bookmark file or stored individually. In yet another alternative embodiment, a 2D or 3D snapshot 208 of the 2D image rendered under the current viewing configuration is also stored with the bookmark. This 2D image may be used to identify the bookmark, such as a "thumbnail" image, or may be used to view the bookmark on an imaging system when the source image data is otherwise unavailable.

As was described above, in one embodiment, the bookmark function 24 captures system inputs at the input level, i.e. the actual input, such as the user interface interact is captured. In an alternate embodiment, the system inputs are captured by the bookmark function 24 at a lower level such as at the application program interface of the system 10 rendering functionality. For example the open graphics library ("OpenGL") or DirectX commands may be captured.

In one embodiment, the bookmark function 24, using the captured system inputs, enhances the user interface of the system 10 and permits a user to undo or repeat system inputs independent of the bookmark function's 24 ability to save bookmarks 200. In this embodiment, the bookmark function 24 captures the system inputs and system parameters 204 as each input is received. This permits the user to return the system 10 to a previous state, i.e. revert the current viewing configuration back to a previous viewing configuration. This is useful, for example, where the user makes a mistake and enters the wrong input or where a user is trying out different inputs to determine an optimal or desired result. Where the user wishes to utilize the same input multiple times, they may "redo" a system input which causes a previously entered system input to be applied again. In an alternate embodiment, the user may selectively choose which system inputs to undo or redo, such as by selecting the particular system input from a displayed list of captured system inputs, alone or in conjunction with the associated state of the system parameters. Alternatively, the bookmark 24 may only allow the user to sequentially undo system inputs.

Once a bookmark 200 has been saved, the user may subsequently retrieve that bookmark to restore the saved viewing configuration, such as for the purpose of resuming an interrupted evaluation, reviewing a completed evaluation or performing additional evaluations of the source image data. In one embodiment, the bookmark 200 is associated with the source image data. In this embodiment, the user indicates, via the input 16, that they wish to retrieve a bookmark 200. The bookmark function 24 receives the input and loads the associated the source image data identified 210 by the selected bookmark from a memory or other storage medium, located locally or remote, e.g. on a network. In embodiments where the source image data is not identified by, or associated with, the bookmark 200, the user may be prompted to provide such an identification or association, including identification of source image data different from that used to create the bookmark. The system 10 then assumes the default viewing configuration, as described above, based on the source image data, the current system characteristics and the current state of the system parameters. The system 10 may or may not display the associated 2D image prior to applying the bookmark. In one embodiment, the source image data is loaded and the bookmark 200 is applied prior to any display of the image data. Once the bookmark 200 has been applied, the resultant restored viewing configuration is displayed. This allows the bookmark function 24, for example, to optimize processing and application of the bookmark 200 to the image data out the view of the user. The bookmark function 24 then applies the bookmark by replaying the captured system inputs 202, each input having its original effect on the system 10 and the current viewing configuration. In one embodiment, the captured system inputs 202 are replayed sequentially. Alternatively, the bookmark function 24 may optimize the playback of system inputs 202, possibly applying them non-sequentially. Where characteristics of the system inputs have also been captured, such as the relative timing of the system inputs, those characteristics may also be replayed. After all of the captured inputs 202 have been replayed, the viewing configuration, including the currently presented 2D image, is identical as to when the bookmark was saved.

Figure 2:
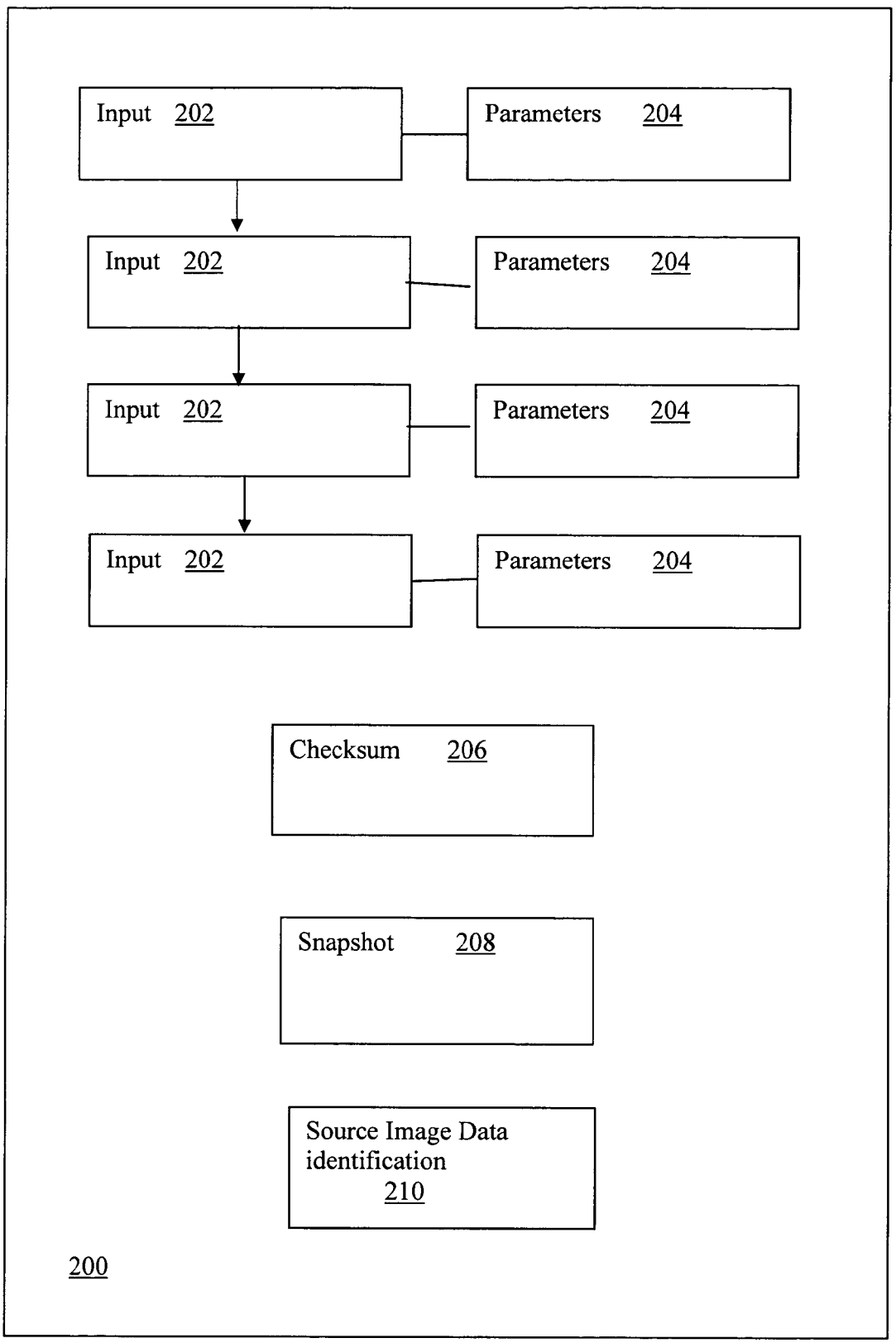
FIG. 2 depicts a block diagram of an exemplary bookmark according to one embodiment.

An exemplary bookmark 200 is schematically illustrated in FIG. 2. The bookmark 200 is shown to include one or more captured system inputs 202. The bookmark 200 may also include system parameters and/or system characteristics 204 captured prior to, or after, each system input 202 has effected its result. In an alternate embodiment, the final state of the system parameters and/or system characteristics may be stored in addition to, or in lieu of, the system parameters and/or system characteristics 204 for each input. In addition, the bookmark 200 may include a 2D or 3D snapshot 208, as described above, a checksum 206, for error detection, described below, and/or identification 210 of the source image data. In one embodiment, bookmarks are stored using extensible markup language ("XML"), though it will be appreciated that other storage formats may be used to store the requisite data. In one embodiment, the bookmark 200 described above defines a single data structure capable of storing snapshots as well as viewing configurations and maintaining the association of the snapshot(s) and viewing configuration(s) with the underlying source image data, whether it be a single 3D volume or multiple 3D volumes (sequential or non-sequential) of a 4D sequence. In this embodiment, the identification field 210 of the bookmark 200 data structure is capable of storing the identity of one or more 3D volumes. In use, the bookmark 200 data structure is populated with data as this data is created by the user. For example, if during manipulation of acquired image data currently stored only in the imaging system 10 acquisition buffer, the user selects to save a snapshot, the bookmark 200 data structure will be populated with the snapshot data. The user may choose to stop and save this bookmark 200 as is, with only the snapshot contained therein. However, if, subsequently, the user chooses to save the acquired source image data from the acquisition buffer, or just a portion thereof, the relevant identification data of the one or more saved 3D volumes is also stored in the bookmark 200, thereby maintaining the association of the bookmark 200 with the saved source image data. Further, or alternatively, if the user then chooses to save a viewing configuration, this data is stored in the bookmark 200 as well. Partially populated bookmarks 200, containing only a snapshot or only a viewing configuration, with or without identifying data of the underlying source image data may be saved. This permits the user to save bookmarks 200 which contain viewing configurations and/or snapshots but which are not associated with any underlying source image data, allowing the user the option of discarding the source image data where it is not needed. In an alternate embodiment, the source image data may also be saved into the bookmark 200 data structure. In one embodiment, the bookmark 200 data structure is a data structure compatible with the DICOM standard described above, and is capable of being stored in the DICOM data storage hierarchy. For example, the bookmark 200 may be stored underneath a particular DICOM "series" of a "study" for a particular "patient."

In one embodiment, the bookmark function 24 may compare the values of system parameters 204 saved with the bookmark 200 against the current values of the system parameters to verify that the system inputs 202 were properly applied. Where the system parameters 204 are captured with each captured system input 202, this verification can occur as each system input 202 is reapplied. In an alternate embodiment, where the bookmark function 24 detects a discrepancy between the captured 204 and actual parameters, the user may be warned or prompted to intervene, or the discrepancy may be automatically resolved. As will be discussed below, such discrepancy checking may be used when replaying a bookmark 200 on a different system 10 than was used to save the bookmark 200 to account for differences in the two systems 10, or errors introduced into the captured stream of system inputs 202. Such discrepancy checking may also be used when replaying the bookmark 200 on the acquiring system, where there has been an intervening modification to that system 10 prior to the replaying of the bookmark 200, such as a system 10 upgrade or maintenance.

In yet another alternative embodiment, the bookmark function 24 permits a user to replay a selected subset of the stored system inputs 202. The selected subset may be comprise a contiguous or non-contiguous sequence of inputs 202, replayed in the captured order or in a user specified order.

During replay of an entire bookmark 200, or subset thereof, the bookmark function 24 may further allow the user to reduce or increase the speed at which the stored system inputs 202 are played back, or manually step the playback of the system inputs 202. This may be useful for debugging an undesirable or unexpected viewing configuration, or otherwise checking for error conditions, by allowing the user to perceive the effect on the viewing configuration of each system input 202 being played back. In one embodiment, the bookmark function 24 may highlight the effect of each system input to make that effect readily apparent to the user, for example, where the actual effect on the viewing configuration is subtle. Control over system input 202 playback may also be useful for training sonographers to use the imaging system 10.

In yet another alternative embodiment, the bookmark function 24 allows the user to edit saved bookmarks 200. Editing may be performed with respect to, or independent of, the source image data used to create the bookmark 200. In this embodiment, the user may access the stored captured inputs 202 and edit those inputs 202 to effect changes when the bookmark is played back. Additionally, automated editing of the bookmark 200 may be provided. In one embodiment, the bookmark function 24 automatically edits a saved bookmark 200 to remove redundant or irrelevant system inputs 202 and/or optimize the sequence of captured system inputs. This may be accomplished by comparing captured system parameters/characteristics associated with each captured input 202 and determining whether or not the captured input 202 actually changed anything. Such comparison may performed between consecutively or non-consecutively captured inputs 202. Further, in the case where a bookmark 200 is transferred to an imaging system different from the imaging system where the bookmark 200 was created, the bookmark 200 may be edited, automatically or manually, to recalibrate or translate those system inputs which are dependent upon the differences between the two systems.

In yet another alternative embodiment, a saved bookmark 200 may be retrieved and applied to source image data that is different from the source image data used to create the bookmark 200. This is useful where the bookmark 200 embodies a generic process or functionality that is independent of the source image data. For example, the user may insert a text notation identifying themselves, their organization, and/or other standardized information, such that such information is displayed in the 2D representation. These inputs represent a viewing configuration which may be saved as a bookmark 200 as described. However, where the user inserts such notations in all of their data, they may reuse this saved bookmark 200 to cause insertion of the notation with any source image data. Once inserted, the user may continue with their evaluation, refining their viewing configuration with specific reference to the particular source image data and then save a new bookmark 200 encompassing both the generic inputs of the previous bookmark and the data specific inputs provided thereafter. In one embodiment, libraries of generic, i.e. source image data independent, bookmarks 200 may be provided which may be used and then tailored to a users specific needs.

As described above, in yet another embodiment, a saved bookmark 200 may be transferred to another imaging system 10 different from the imaging system 10 used to create the bookmark 200. The saved bookmark 200 may be communicated between the systems 10 using a network 32 or via removable storage media 26, or other medium. A bookmark 200 may be transferred with or without the underlying source image data used to create the bookmark 200. This permits a user to continue an evaluation on a machine that is different from the one on which it was started. Where a bookmark 200 is transferred without the underlying source image data, the source image identification data 210 within the bookmark 200 permits the receiving system 10 to locate and load the image data via the network 32 from wherever the source image data is currently located. For example, if the sonographer begins their evaluation on the imaging system 10 in which the source image data was acquired, they may have to interrupt their evaluation if the system 10 is needed for another examination. In this embodiment, the sonographer may bookmark 200 the current viewing configuration and transfer the bookmark 200 and underlying source image data to another imaging system 10, such an imaging review workstation, where they can resume their evaluation from where the left off. In one embodiment, the bookmark function 24 on the receiving machine determines if there are differences between the sending and receiving imaging systems 10 and automatically recalibrates the bookmark 200 accordingly, or prompts the user, to account for the differences, i.e. compensate for errors or quantization effects introduced into the stored system inputs due to the system 10 differences. This determination may be based on a checksum value stored with the bookmark 200, described in more detail below. In an alternate embodiment, such discrepancy checking and recalibration is performed on the sending system 10 prior to transferring the bookmark 200. Where the receiving system 10 utilizes rendering functionality different from the rendering functionality of the sending system, the bookmark function 24, of either the sending or receiving system 10, may translate the stored system inputs into inputs comprehensible by the receiving system's 10 rendering functionality. Further, where the captured system inputs of the bookmark include captured user interface interactions, the bookmark function 24 may translate the stored system inputs into inputs compatible with the user interface of receiving system 10. For example, where mousing events are captured between two displayed graphic user interface elements, mousing distances may be automatically updated where those distances different between the user interfaces of the two systems 10.

In one embodiment, the bookmark 200 may include a checksum value 206 which permits the bookmark function 24 to account for any mis-calibration or quantization effects in the transfer of the bookmark 200, or replay of the bookmark 200 on a system 10 that has been modified since the creation of the bookmark 200. In one embodiment, this checksum value 206 is created and stored when the bookmark 200 is saved based on the current 2D image being displayed, or snapshot thereof. When the bookmark 200 is retrieved and reapplied, the checksum value of the resultant displayed 2D image or snapshot is computed again and compared with the stored value to determine if an error has occurred. The checksum value 206 may be computed based on the raw pixel data of the snapshot. In an alternate embodiment, a checksum value 206 may be computed as each system input 202 is received, applied to the source image data and recorded. Upon replay of the bookmark 200, the checksum 206 is verified for each replayed system input 202 permitting errors to be immediately detected and isolated to the offending system input 202. Such errors may be automatically corrected or presented to the user to take appropriate action. In an alternate embodiment, this checksum value 206 is created when the bookmark 200 is saved based on the current system inputs and system characteristics and/or system parameters and stored with the bookmark 200. The checksum value 206 is then recomputed, as described, when the bookmark 200 is retrieved and compared to the stored value 206 to determine if an error has been introduced.

The disclosed embodiments permit a user to retrieve a saved viewing configuration, including the resultant displayed 2D image, of particular source image data in the viewing configuration that was set when the 2D image of interest was composed. This feature increases work-flow flexibility by allowing the user to return to work that was previously suspended or terminated without the need to reset the viewing parameters to manipulate the image data to the last configuration set. By saving the system inputs used to create the viewing configuration, there is no need to save the current values of the system parameters since the viewing configuration is a result of the application system inputs to the system characteristics and default system parameters.

The disclosed embodiments further permit the user to save a particular viewing configuration without altering the underlying source image data. This permits the user to undo changes and revert back to the original data and also allows others to use the unaltered image data.

The imaging system 10 is configured such that the bookmark 200 saving procedure is independent of the saving procedure for the underlying image data. That is, saving the bookmark 200 does not depend on whether the underlying image data has been saved. Since a 3D ultrasound volume or 4D sequence is quite large and takes a substantial amount of time to save, the system allows the user to independently decide whether or not to save the image data. Thus, the image data may be saved before or after the bookmark 200 has been saved, and may not even be saved. Regardless of whether the image data has been saved, the bookmark 200 may contain a snapshot 208 and the information 210 that identifies the image data from which the snapshot was derived. This implies that a relationship between the image data and the bookmark may or may not exist. Unlike conventional ultrasound imaging systems in which the relationship information is stored in a database, the relationship information need not be stored by the system 10. Instead, the relationship information may be inferred at runtime by reading the identifying information 210 from the bookmark 200 and determining whether the underlying image data is available.

In one embodiment, the bookmark function 24 includes an event recorder which is coupled with the application program interface of the rendering functionality of the system 10 as well as the operating system. This permits the bookmark function 24 to access all system characteristics, system parameters as well as all system inputs directed to the rendering functionality or to the system 10 in general.

In yet another alternative embodiment, bookmarks related to 4D sequences may be created. As discussed above, a 4D sequence includes image data characterized by at least four parameters of interest, such as a collection of 3D volumes associated by time, and typically, further associated by having been acquired during a single examination. The 4D sequence is typically characterized by the ability to depict changes and/or movement over time, or other quantification, of the imaged structures, or depict structures larger than the field of view of a single 2D image or 3D volume. As described above, the disclosed embodiments further relate to method of storing bookmarks 200, the content of which is context dependent. As used herein, a "3D bookmark" is a bookmark 200, as described above, which is related to single 3D volume. A "4D bookmark" is a bookmark 200 relating to a 4D sequence.

A 4D bookmark 200 may contain only the resultant system parameters and/or system characteristics which result from user manipulation of the 4D sequence. Further, 4D bookmarks 200 may contain data specific to 4D sequence, such as user indications of beginning, ending and primary 3D volumes in the sequence, or subset thereof.

The bookmark function 24 is further capable of saving bookmarks 200 based on the context of the system 10 state at the time the user saves the bookmark 200. For example, if the user saves a bookmark but fails to save the source image data, the bookmark function 24 may only save the snapshot information, if the user does not wish to save an image data independent bookmark 200. If the user saves only a single 3D volume, the bookmark function 24 may create only a 3D bookmark, and if the user saves an entire sequence of 3D volumes, the bookmark function 24 may create a 4D bookmark.

In one embodiment, the bookmark function 24 creates bookmarks 200 in a format compatible with the DICOM image format. DICOM, as described above, is a standard imaging data format for diagnostic medical imaging data. Under DICOM, image data is stored in a hierarchical file system based on the patient. Within each patient's hierarchy, one or more studies are created, each study containing one or more series, each of which may contain one or more 2D images, 3D volumes and or 4D sequences.

In operation, a user acquires one or a sequence of 3D volumes. When the user elects to save the acquired data, a new series is created under the current study for the current patient (which may need to be created if this is a new study and/or patient). The user then reviews and manipulates the acquired data. During manipulation of a 4D sequence, the user may mark a particular 3D volume as a beginning volume and another particular 3D volume as an ending volume within the sequence of volumes. This effectively creates a new series within the study file. If the buffered image data is flushed, all unsaved manipulations, i.e. unsaved bookmarks, are flushed as well. In this embodiment, the existing DICOM data storage framework can be used to support bookmarks 200 according to the disclosed embodiments by storing those bookmarks 200 as new series within the DICOM image data hierarchy. It will be appreciated however, that the disclosed embodiments may be implemented with other data storage formats.

It is therefore intended that the foregoing detailed description be regarded as illustrative rather than limiting, and that it be understood that it is the following claims, including all equivalents, that are intended to define the spirit and scope of this invention.

We claim:

1. A method of managing image data acquired with a first diagnostic medical imaging system, said first diagnostic medical imaging system comprising a display, said image data comprising a first arrangement, said method comprising:
    displaying said image data on said display, said displayed image data having a second arrangement based on said first arrangement;
    receiving a sequence of inputs, said sequence of inputs operative to manipulate said displayed image data from said second arrangement to a third arrangement, without substantially altering said first arrangement; and
    recording said sequence of inputs, said recorded sequence of inputs being capable of being automatically applied to said displayed image data having said second arrangement to realize said third arrangement without substantially altering said first arrangement.

2. The method of claim 1, further comprising:
    storing said recorded sequence of inputs separate from said image data.

3. The method of claim 1, further comprising:
    redisplaying said image data, said redisplayed image data having said second arrangement;
    receiving direction from a user to replay said recorded sequence of inputs; and
    replaying, in response to said direction, said recorded sequence of inputs without further input from said user to manipulate said redisplayed image data from said second arrangement to said third arrangement, without substantially altering said first arrangement.

4. The method of claim 3, further comprising:
    communicating said recorded sequence of inputs from said first diagnostic medical imaging system to a second diagnostic medical imaging system located remote from said first diagnostic medical imaging system, said redisplaying, receiving and replaying occurring on said second diagnostic medical imaging system.

5. The method of claim 4, wherein said replaying further comprises:
    determining at least one difference between said first diagnostic medical imaging system and said second diagnostic medical imaging system; and
    reporting to said user if at least one input of said recorded sequence of inputs depends upon said difference.

6. The method of claim 4, wherein said replaying further comprises:
    adjusting at least one input of said recorded sequence of inputs to compensate for differences between said first diagnostic medical imaging system and said second diagnostic medical imaging system.

7. The method of claim 1, further comprising:
    allowing said recorded sequence of inputs to be altered; and
    re-manipulating said displayed image to a fourth arrangement based on said altered recorded sequence of inputs, without substantially altering said first arrangement.

8. The method of claim 7, wherein said re-manipulating further comprises:
    reverting said displayed image back to said second arrangement; and
    replaying said altered recorded sequence of inputs to manipulate said displayed image from said second arrangement to said fourth arrangement.

9. The method of claim 7, wherein said allowing further comprises allowing a user to one of add an input to said recorded sequence of inputs, remove an input from said recorded sequence of inputs and modify an input of said recorded sequence of inputs.

10. The method of claim 1, wherein said image data comprises a three dimensional volume.

11. The method of claim 10, wherein said image data comprises a sequence of three dimensional volumes, each three dimensional volume of said sequence of three dimensional volumes having been incrementally acquired over a period of time.

12. The method of claim 1, wherein said first diagnostic medical imaging system comprises a diagnostic medical ultrasound system.

13. The method of claim 12, wherein said sequence of inputs comprises at least one input received from a user via a user interface coupled with said first diagnostic medical imaging system.

14. The method of claim 1, wherein said first and second arrangements each comprise at least one of composition, position, organization, annotation, augmentation, transformation, and rotation of said displayed image data.

15. The method of claim 1, wherein said first diagnostic medical imaging system comprises a plurality of display parameters, each of said display parameters comprising a value, wherein said second arrangement is further based on said value of each of said display parameters, at least one said sequence of inputs being operative to alter said value of at least one display parameter to realize said third arrangement, said recording further comprising recording at least said altered value, wherein said recorded altered value is capable of being applied, in conjunction with said recorded sequence of inputs, to said displayed image data having said second arrangement to realize said third arrangement without substantially altering said first arrangement.

16. The method of claim 1, wherein said recording further includes automatically recording said sequence of inputs prior to loss of function of said first diagnostic medical imaging system, said method further comprising applying said recorded sequence of inputs upon restoration of said function of said first diagnostic medical imaging system.

17. The method of claim 1, wherein said recording further comprises recording an identification of said image data with said sequence of inputs.

18. A method of managing image data acquired with a first diagnostic medical imaging system, said first diagnostic medical imaging system comprising a display and a plurality of display parameters, each of said display parameters further comprising a value, said value of each of said plurality of display parameters operative to control an arrangement of said image data as displayed on said display, said method comprising:
    displaying said image data on said display, said displayed image data comprising a sequence of three dimensional volumes, each three dimensional volume of said sequence of three dimensional volumes having been incrementally acquired over a period of time, said displayed image data further having a first arrangement displayed on said display based on said image data and at least one of said values of said plurality of display parameters;

receiving input operative to alter said value of at least one of said plurality of display parameters, whereby said displayed image is manipulated from said first arrangement displayed on said display to a second arrangement displayed on said display based on said altered value, without substantially altering said image data; and recording at least said altered value, wherein said recorded altered value is capable of being automatically applied to said displayed image data having said first arrangement to realize said second arrangement on said display without substantially altering said image data.

19. The method of claim 18, further comprising:
storing said recorded altered value separate from said image data.

20. The method of claim 18, further comprising:
loading said image data, said loaded image data having said first arrangement;
receiving direction from a user to apply said recorded altered value; and
applying, in response to said direction, said recorded altered value without further input from said user to manipulate said loaded image data from said first arrangement to said second arrangement displayed on said display, without substantially altering said image data.

21. The method of claim 20, further comprising:
communicating said recorded altered value from said first diagnostic medical imaging system to a second diagnostic medical imaging system located remote from said first diagnostic medical imaging system, said loading, receiving and applying occurring on said second diagnostic medical imaging system.

22. The method of claim 21, wherein said applying further comprises:
determining at least one difference between said first diagnostic medical imaging system and said second diagnostic medical imaging system; and
reporting to said user if at least one altered value of said recorded altered value depends upon said difference.

23. The method of claim 21, wherein said applying further comprises:
adjusting at least one of said recorded altered value to compensate for differences between said first diagnostic medical imaging system and said second diagnostic medical imaging system.

24. The method of claim 18, further comprising:
allowing said recorded altered value to be modified; and
re-manipulating said displayed image to a third arrangement based on said modified recorded altered value, without substantially altering said image data.

25. The method of claim 24, wherein said re-manipulating further comprises:
reverting said displayed image back to said first arrangement; and
re-applying said modified recorded altered value to manipulate said displayed image from said first arrangement to said third arrangement.

26. The method of claim 24, wherein said allowing further comprises allowing a user to one of add to said recorded altered value, remove from said recorded altered value and modify said recorded altered value.

27. The method of claim 18, wherein said first diagnostic medical imaging system comprises a diagnostic medical ultrasound system.

28. The method of claim 18, wherein said first diagnostic medical imaging system comprises a review workstation.

29. The method of claim 18, wherein said first and second arrangements each comprise at least one of composition, position, organization, annotation, augmentation, transformation, and rotation of said displayed image data.

30. The method of claim 18, wherein said receiving further comprises receiving a sequence of inputs from a user via a user interface coupled with said first diagnostic medical imaging system, whereby said displayed image is further manipulated from said first arrangement to said second arrangement based on said sequence of inputs, said recording further comprising recording said sequence of inputs, wherein said recorded sequence of inputs is capable of being automatically applied to said displayed image data having said first arrangement in conjunction with said recorded altered value to realize said second arrangement.

31. The method of claim 18, wherein said recording further comprises recording an identification of said image data with said at least said altered value.

32. In a first diagnostic medical imaging system having a first display for displaying image data controllable by a first plurality of display parameters, said image data comprising a sequence of three dimensional volumes, each of said three dimensional volumes having been incrementally acquired over a period of time, a method of managing said image data, said method comprising:
allowing a user to manipulate at least one of said first plurality of display parameters to define a viewing configuration of a portion of said image data on said first display without substantially altering said image data; and
storing said user defined viewing configuration independent of said image data, without substantially altering said image data, whereby said stored user defined viewing configuration is capable of being retrieved to recreate said user defined viewing configuration of said image data.

33. The method of claim 32, wherein said allowing further comprises receiving a sequence of inputs, said sequence of inputs operative to manipulate said first plurality of display parameters, said user defined viewing configuration comprising said sequence of inputs.

34. The method of claim 32, wherein said user defined viewing configuration comprises at least said manipulated at least one of said first plurality of display parameters.

35. The method of claim 32, wherein said stored user defined viewing configuration is capable of being communicated to a second diagnostic medical imaging system, said second diagnostic medical imaging system having a second display controllable by a second plurality of display parameters, said communicated stored user defined viewing configuration being operative to manipulate at least one of said second plurality of display parameters to recreate said user defined viewing configuration of said image data on said second display.

36. The method of claim 32, wherein said storing further includes automatically storing said user defined viewing configuration prior to loss of function of said first diagnostic medical imaging system, said method further comprising restoring said user defined viewing configuration to recreate said user defined viewing configuration of said image data upon restoration of said function of said first diagnostic medical imaging system.

37. The method of claim 32, wherein said storing further includes storing identification of said image data with said user defined viewing configuration.

38. An apparatus for managing image data acquired with a first diagnostic medical imaging system, said first diagnostic medical imaging system comprising a first display, said image data comprising a first arrangement, said apparatus comprising:
   first display logic coupled with said first display and operative to display said image data on said first display having a second arrangement as a function of said first arrangement;
   first input logic coupled with said first display logic and operative to receive a sequence of inputs, said sequence of inputs operative to cause said first display logic to manipulate said displayed image data from said second arrangement to a third arrangement displayed on said first display without substantially altering said first arrangement; and
   first store logic coupled with said first display logic and said first input logic and operative to store said received sequence of inputs in a first memory coupled with said first store logic, said stored sequence of inputs capable of being retrieved from said first memory and automatically applied to said first display logic to cause said first display logic to manipulate said displayed image data having said second arrangement to realize said third arrangement displayed on said first display without substantially altering said first arrangement.

39. The apparatus of claim 38, wherein:
   said first display logic is further operative to redisplay said image data, said redisplayed image data having said second arrangement;
   said first input logic is further operative to receive direction from a user to replay said stored sequence of inputs; and
   said first store logic is further operative to retrieve said stored sequence of inputs from said first memory and apply said stored sequence of inputs to said first display logic to cause said first display logic to manipulate said displayed image data having said second arrangement to realize said third arrangement on said first display without substantially altering said first arrangement.

40. The apparatus of claim 38, wherein said apparatus further comprises:
   first communication logic coupled with said first store logic and operative to transmit said stored sequence of inputs to a second diagnostic medical imaging system via a network coupled between said first and second diagnostic medical imaging systems, said second diagnostic medical imaging system comprising a second display, second display logic with said second display, second input logic coupled with said second display logic, second store logic coupled with said second display logic and said second input logic, and second communications logic coupled with said second store logic, said second communications logic operative to receive said transmitted stored sequence of inputs and store said transmitted stored sequence of inputs in a second memory coupled with said second store logic, and wherein:
   said second display logic is further operative to redisplay said image data, said redisplayed image data having said second arrangement;
   said second input logic is further operative to receive direction from a user to replay said transmitted stored sequence of inputs; and
   said second store logic is further operative to retrieve said transmitted stored sequence of inputs from said second memory and apply said received sequence of inputs to said second display logic to cause said second display logic to manipulate said displayed image data having said second arrangement to realize said third arrangement on said second display without substantially altering said first arrangement.

41. The apparatus of claim 40, wherein said second store logic is further operative to determine at least one difference between said first diagnostic medical imaging system and said second diagnostic medical imaging system; and
   report to said user if at least one input of said transmitted stored sequence of inputs depends upon said difference.

42. The apparatus of claim 40, wherein said second store logic is further operative to adjust at least one input of said transmitted stored sequence of inputs to compensate for differences between said first diagnostic medical imaging system and said second diagnostic medical imaging system.

43. The apparatus of claim 38, wherein said first store logic is operative to allow said stored sequence of inputs to be altered, wherein said first store logic is further operative to apply said altered stored sequence of inputs to said first display logic to cause said first display logic to re-manipulate said displayed image to a fourth arrangement on said first display based on said altered stored sequence of inputs, without substantially altering said first arrangement.

44. The apparatus of claim 38, wherein said first diagnostic medical imaging system comprises a diagnostic medical ultrasound system.

45. The apparatus of claim 38, wherein said first diagnostic medical imaging system comprises a plurality of display parameters, each of said display parameters comprising a value, wherein said second arrangement is further based on said value of each of said display parameters, at least one said sequence of inputs being operative to alter said value of at least one display parameter to realize said third arrangement, said first store logic being further operative to store at least said altered value, wherein said stored altered value is capable of being applied, in conjunction with said stored sequence of inputs, to said first display logic to cause said first display logic to manipulate said displayed image data having said second arrangement to realize said third arrangement on said first display without substantially altering said first arrangement.

46. The apparatus of claim 38, wherein said first store logic is further operative to store identification of said image data in said first memory with said received sequence of inputs.

47. An apparatus for managing image data acquired with a first diagnostic medical imaging system, said first diagnostic medical imaging system comprising a first display and a first plurality of display parameters, each of said display parameters further comprising a value, said value of each of said first plurality of display parameters operative to control an arrangement of said image data as displayed on said display, said apparatus comprising:
   first display logic coupled with said first display and operative to display said image data on said first display, said displayed image data comprising a sequence of three dimensional volumes, each three dimensional volume of said sequence of three dimensional volumes having been incrementally acquired over a period of time, said displayed image data further having a first arrangement displayed on said display based on said image data and at least one of said values of said first plurality of display parameters;

first input logic coupled with said first display and operative to receive input, said input operative to alter said value of at least one of said first plurality of display parameters, whereby said first display logic is operative to manipulate said displayed image data from said first arrangement displayed on said display to a second arrangement displayed on said display based on said altered value, without substantially altering said image data; and first store logic coupled with said first input logic and said first display logic and operative to store at least said altered value in a first memory coupled with said first store logic, wherein said stored altered value is capable of being automatically applied to said displayed image data having said first arrangement to realize said second arrangement on said display without substantially altering said image data.

48. The apparatus of claim 47, wherein:
said first display logic is further operative to load said image data, said loaded image data having said first arrangement;
said first input logic is further operative to receive direction from a user to apply said recorded altered value; and
said first store logic is further operative to retrieve said stored altered value from said first memory in response to said direction and apply said recorded altered value without further input from said user to cause said first display logic to manipulate said loaded image data from said first arrangement to said second arrangement displayed on said display, without substantially altering said image data.

49. The apparatus of claim 47, wherein said apparatus further comprises:
first communication logic coupled with said first store logic and operative to transmit said stored altered value to a second diagnostic medical imaging system via a network coupled between said first and second diagnostic medical imaging systems, said second diagnostic medical imaging system comprising a second display, second display logic with said second display, second input logic coupled with said second display logic, second store logic coupled with said second display logic and said second input logic, and second communications logic coupled wit said second store logic, said second communications logic operative to receive said transmitted stored altered value and store said transmitted stored altered value in a second memory coupled with said second store logic, and wherein:
said second display logic is further operative to load said image data, said loaded image data having said first arrangement;
said second input logic is further operative to receive direction from a user to apply said transmitted stored altered value; and
said second store logic is further operative to retrieve said transmitted stored altered value from said second memory and apply said received altered value to said second display logic to cause said second display logic to manipulate said displayed image data having said first arrangement to realize said second arrangement on said second display without substantially altering said image data.

50. The apparatus of claim 49, wherein said second store logic is further operative to determine at feast one difference between said first diagnostic medical imaging system and said second diagnostic medical imaging system; and
report to said user if at least one value of said transmitted stored altered value depends upon said difference.

51. The apparatus of claim 49, wherein said second store logic is further operative to adjust at least one value of said transmitted stored altered value to compensate for differences between said first diagnostic medical imaging system and said second diagnostic medical imaging system.

52. The apparatus of claim 47, wherein said first store logic is operative to allow said stored altered value to be modified, wherein said first store logic is further operative to apply said modified stored altered value to said first display logic to cause said first display logic to re-manipulate said displayed image to a third arrangement on said first display based on said modified stored altered value, without substantially altering said image data.

53. The apparatus of claim 47, wherein said first diagnostic medical imaging system comprises a diagnostic medical ultrasound system.

54. The apparatus of claim 47, wherein said first diagnostic medical imaging system comprises a review workstation.

55. The apparatus of claim 47, wherein said first store logic is further operative to store identification of said image data in said first memory with said at least said altered value.

56. In a first diagnostic medical imaging system having a first display for displaying image data controllable by a first plurality of display parameters, an apparatus for managing said image data, said image data comprising a sequence of three dimensional volumes, each of said three dimensional volumes having been incrementally acquired over a period of time, said apparatus comprising:
means for allowing a user to manipulate at least one of said first plurality of display parameters to define a viewing configuration of a portion of said image data on said first display without substantially altering said image data; and
means for storing said user defined viewing configuration independent of said image data, without substantially altering said image data, whereby said stored user defined viewing configuration is capable of being retrieved to recreate said user defined viewing configuration of said portion of said image data.

57. The apparatus of claim 56, wherein said means for allowing further comprises means for receiving a sequence of inputs, said sequence of inputs operative to manipulate said first plurality of display parameters, said user defined viewing configuration comprising said sequence of inputs.

58. The apparatus of claim 56, wherein said stored user is capable of being communicated to a second diagnostic medical imaging system, said second diagnostic medical imaging system having a second display controllable by a second plurality of display parameters, said communicated stored user defined viewing configuration being operative to manipulate at least one of said second plurality of display parameters to recreate said user defined viewing configuration of said image data on said second display.

59. The apparatus of claim 56, wherein said means for storing further comprises means for identifying said image data and means for storing said identification with said user defined viewing configuration.

* * * * *